July 11, 1972 W. A. WARRINER Plant Pat. 3,234
ROSE PLANT
Filed Jan. 6, 1971
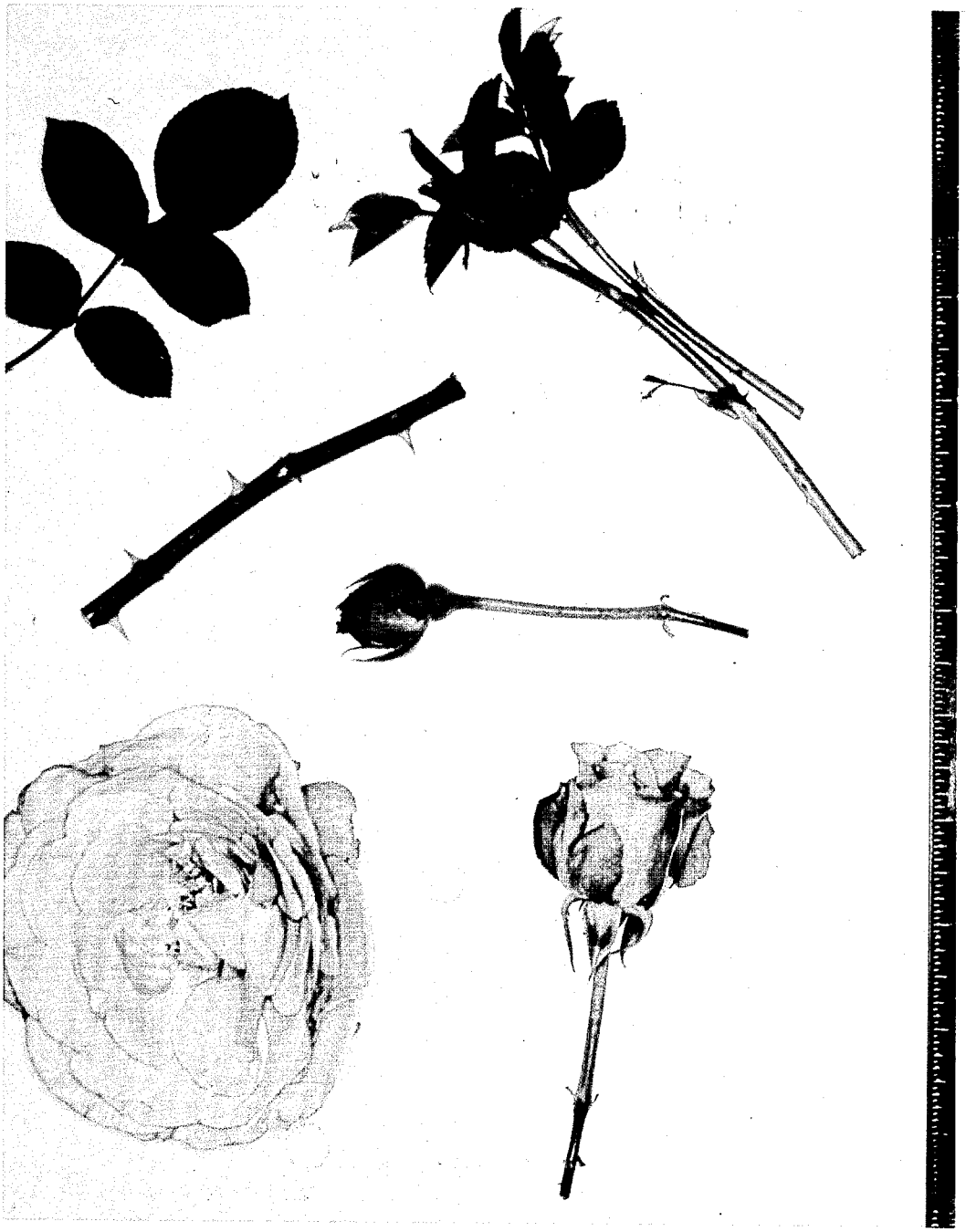
WILLIAM A. WARRINER
INVENTOR
BY
BUCKHORN, BLORE, KLARQUIST & SPARKMAN
ATTORNEYS

United States Patent Office

Plant Pat. 3,234
Patented July 11, 1972

3,234
ROSE PLANT

William A. Warriner, Tustin, Calif., assignor to Jackson & Perkins Company, Medford, Oreg.

Filed Jan. 6, 1971, Ser. No. 104,525
Int. Cl. A01h *5/00*
U.S. Cl. Plt.—19 1 Claim

The present invention relates to a new and distinct variety of rose plant of the hybrid tea class originated by me by crossing two unnamed hybrid tea varieties.

The primary objective of this breeding was to produce a new and improved variety of the hybrid tea class bearing freely large flowers in the "lilac" to "lavender" color range.

This objective was achieved along with other desirable improvements as evidenced by the following unique combination of characteristics which are outstanding in the new variety, and which distinguish it from its parents as well as from all other varieties of which I am aware:

(1) An upright, but heavily branched habit of growth.
(2) An unusually free blooming habit.
(3) Flowers borne singly and often in clusters of three or four blooms.
(4) A distinctive flower color from Tyrian Purple in the bud to Persian Rose in the fully opened flower.
(5) A very strong, pleasant "tea" fragrance.

Asexual reproduction of my new variety by budding as performed at Wasco, Calif., shows that the aforementioned characteristics and distinctions come true to form and are established and transmitted through succeeding propagations.

The accompanying drawing shows typical specimens of the vegetative growth and flowers of my new variety in different stages of development, depicted in color as nearly true as it is reasonably possible to make the same in a color illustration of this character.

The following is a detailed description of my new variety with color terminology in accordance with Wilson's "Horticultural Color Chart," except where ordinary dictionary significance of color is indicated.

Parentage: Seedling.
*Seed parent.*—An unnamed variety.
*Pollen parent.*—An unnamed variety.
Classification:
*Botanic.*—*Rosa hybrid.*
*Commercial.*—Hybrid tea.

*Flower*

(Observations were made in mid-November in the afternoon at Irvine, California of outdoor grown flowers.)

Blooming habit: Recurrent—continuous.
Bud:
*Size.*—Medium (1" to 1½").
*Form.*—Pointed, ovoid.
*Color.*—When sepals first divide—Oxblood Red (00823). When half blown—inside of petals—Tyrian Purple (727); reverse of petals—near Magenta (27).
*Sepals.*—Color: Inside: near Lettuce Green (861)—slightly tomentose. Outside: Slightly lighter than Spinach Green (0960/3). Three appendaged sepals lightly appendaged. Two unappendaged sepals smooth edged.

*Receptacle.*—Color: Lettuce Green (861). Shape: funnel. Size: small. Surface: smooth.
*Peduncle.*—Length: Short. Surface: Prickly. Color: Lettuce Green (861), overlaid with Garnet Brown (00918/3) on side exposed to sun. Strength: Stiff, erect, slender.
*Opening.*—Petals roll outward, not spiral opening.
Bloom:
*Size.*—Large (4" to 4½").
*Borne.*—Singly and several together.
*Stems.*—Medium, normal strength.
*Form.*—When first open—cupped. Permanence—retains its form to the end. Petals curl back very little.
*Petalage.*—From 30 to 35.
*Color.*—Center of flower: Upper side of petals—Persian Rose (628/1). Reverse side of petals—Persian Rose (628/3). Outer petals: Upper side of petals—same as center petals. Reverse of petals: same as center petals. Base of petals: small area of Primrose Yellow (601). General tonality from a distance—Persian Rose (628/1). No variegations.
*Discoloration.*—General tonality at the end of first day—Persian Rose (628/1). Third day—Persian Rose (628/1) with outer edges darkening to Persian Rose (628).
*Fragrance.*—Strong. Nature—tea.
Petals:
*Texture.*—Leathery.
*Surface.*—Inside—satiny. Reverse—satiny.
*Shape.*—Oval.
*Form.*—Tips slightly recurved.
*Arrangement.*—Slightly irregular.
*Petaloids in center.*—Few.
*Persistence.*—Drop off cleanly.
*Lastingness.*—On the plant—long. As cut flower—long.
Reproductive parts:
*Stamens, anthers.*—Large, few; regularly arranged around styles. Color—yellow.
*Stamens, filaments (threads).*—Long. Color—reddish brown.
*Pollen.*—Color—white.
*Styles.*—Loosely separated, of even length.
*Stigmas.*—Color—yellow.
*Ovaries.*—All enclosed in calyx.

*Plant*

Form: Bush.
Growth: Very vigorous; upright; branching.
Foliage: Compound of 5 leaflets.
*Size.*—Medium.
*Quantity.*—Normal.
*Color.*—New Foliage: Lettuce Green (861/3) near base, overlaid as leaves unfold with large areas of Garnet Brown (00918/3). Old Foilage: Upper side: Parsley Green—(00962): Lower side: Spinach Green—(0960/3).
*Leaflets.*—Shape — Oval pointed. Texture — upper side—leathery; under side—smooth; ribs and veins—ordinary. Edge—serrated. Serration—single; small. Petiole—Rachis—color—green; under side—prickles. Stipules—long; smooth. Disease Resistance—Resistant to mildew under normal growing conditions at Irvine, Calif.

Wood:

*New wood.*—Color—Lettuce Green (861). Bark—smooth.

*Old wood.*—Color—slightly darker than Lettuce Green (861). Bark—smooth.

Thorns:

*Quantity.*—On main stalks from base—ordinary. On laterals from stalk—ordinary.

*Form.*—Narrow base; long; straight.

*Color when young.*—Red.

*Position.*—Irregular.

*Prickles.*—Quantity: On main stalks—few; on laterals—few.

*Short Needles.*—Quantity: On main stalks—few; on laterals—few.

I claim:

1. A new and distinct variety of rose plants of the hybrid tea class substantially as herein shown and described, characterized particularly as to novelty by the unique combination of a bud of Tyrian Purple opening to a flower of Persian Rose; a very strong fragrance of the "tea" type; and an unusual abundance of blooms.

No references cited.

ROBERT E. BAGWILL, Primary Examiner